United States Patent [19]
Weichert et al.

[11] Patent Number: 5,438,408
[45] Date of Patent: Aug. 1, 1995

[54] MEASURING DEVICE AND METHOD FOR THE DETERMINATION OF PARTICLE SIZE DISTRIBUTIONS BY SCATTERED LIGHT MEASUREMENTS

[75] Inventors: Reiner Weichert; Wolfgang Witt, both of Clausthal-Zellerfeld, Germany

[73] Assignee: Sympatec GmbH System-Partikel-Technik, Germany

[21] Appl. No.: 983,559

[22] PCT Filed: June 5, 1992

[86] PCT No.: PCT/EP92/01276

§ 371 Date: Feb. 5, 1993

§ 102(e) Date: Feb. 25, 1993

[87] PCT Pub. No.: WO92/21955

PCT Pub. Date: Dec. 10, 1992

[51] Int. Cl.[6] ............................................. G01N 15/02
[52] U.S. Cl. .................................... 356/336; 356/337
[58] Field of Search ............... 356/336, 337, 338, 339, 356/340, 343

[56] References Cited

U.S. PATENT DOCUMENTS

| | | | |
|---|---|---|---|
| 4,052,600 | 10/1977 | Wertheimer | 364/554 |
| 4,797,923 | 1/1989 | Clarke | 381/31 |
| 5,007,737 | 4/1991 | Hirleman, Jr. | 356/330 |

FOREIGN PATENT DOCUMENTS

| | | |
|---|---|---|
| 0391682 | 4/1990 | European Pat. Off. |
| 0434352 | 6/1991 | European Pat. Off. |
| 2203542 | 4/1988 | United Kingdom . |
| 8900286 | 1/1989 | WIPO . |
| 9201276 | 6/1991 | WIPO . |

OTHER PUBLICATIONS

*Optical Engineering*, vol. 24, No. 6, Nov. 1985, pp. 1060–1065, K. D. Ahlers et al., "Microcomputer based digital image processing system developed to count and size laser-generated small particle images".

*Applied Optics*, vol. 28, No. 22, 15 Nov. 1989, pp. 4870–4878, E. D. Hirleman et al., "Adaptive Fraunhofer diffraction particle sizing instrument using a spatial light modulator".

*Primary Examiner*—Robert P. Limanek
*Assistant Examiner*—David B. Hardy
*Attorney, Agent, or Firm*—Webb Ziesenheim Bruening Logsdon Orkin & Hanson

[57] ABSTRACT

For the determination of fine particle size distributions by scattered light measurements, an assembly of suspended particles is illuminated with coherent light, the scattered light pattern is focused on a light sensitive multi-element detector of a registration device and is transformed there to electrical signals. From the digitized electrical signals, the particle size distribution is computed with a computer. For the simplification of the setup and for the improvement of the accuracy of the computable particle size distribution, it is provided that the registration device is a video camera and that the particle size distribution is computed via the solution of a Fredholm integral equation from the signals produced by the light intensities at the pixels of the video camera. The video camera is a CCD camera. For the variation of the brightness, a rotating disc with gray filters of different transmittivities is provided in the measuring light beam, or the camera is equipped with an electronic shutter for different exposure times. Different fractions of particle sizes is measured also by variation of the angle between the optical axes of illumination and imaging devices.

13 Claims, 6 Drawing Sheets

Fig. 3a
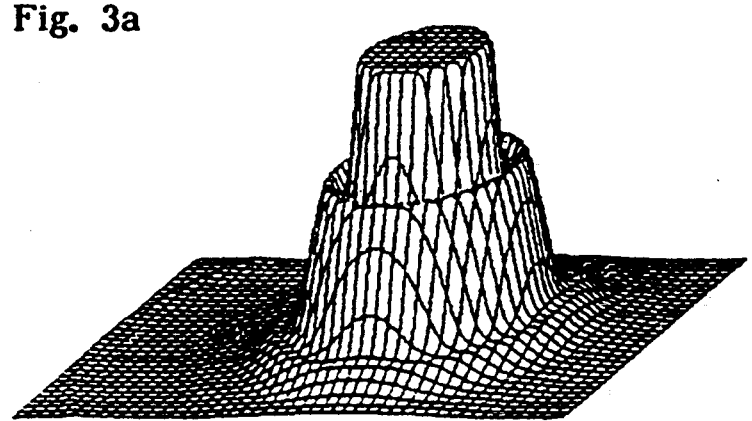
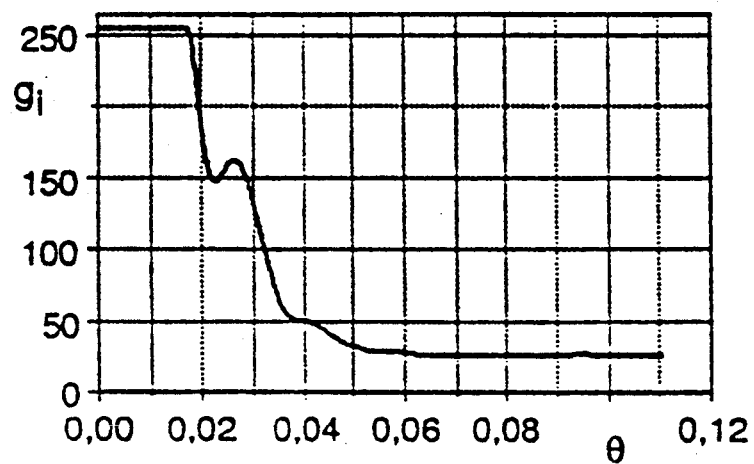
Fig. 3b

MEASURING DEVICE AND METHOD FOR THE DETERMINATION OF PARTICLE SIZE DISTRIBUTIONS BY SCATTERED LIGHT MEASUREMENTS

FIELD OF THE INVENTION

This invention relates to a measuring device and a method for the determination of size distributions of fine particles, especially in the range from 1 to 1000 $\mu$m, by scattered light measurements.

BACKGROUND OF THE INVENTION

In scattered red light measurements, an assembly of suspended particles, e.g. in a cuvette, is illuminated by coherent light. The resulting pattern of scattered light is focused on a light sensitive multi-element detector, which transforms light into electrical signals, From these digitized signals the particle size distribution is calculated by a computer via the solution of a Fredholm integral equation.

Devices for the determination of particle size distributions by mathematical analysis of measured scattered light intensities utilize, among others, laser diffraction instruments or Fraunhofer diffraction instruments. There, an assembly of fine particles is illuminated by monochromatic light of a laser or a laser diode. Each individual illuminated particle of the size x produces a pattern $M(x,\ominus)$ of scattered light, where $\ominus$ is the scattering angle. $M(x,\ominus)$ is either known from theory (Fraunhofer approximation or Mie theory) or can be determined experimentally. The pattern of scattered light being produced by an assembly of particles is the superposition of the patterns of all individual particles. That pattern, depending on the scattering angle $\ominus$, can be registered as light intensity $I(\ominus)$ by a device which is described below.

The computation of the to be measured particle size distribution $Q(x)$ of the assembly of particles is carried out by the solution of a Fredholm integral equation by a computer, which is connected to the registration device. Another known mathematical method is the regularisation according to Phillips-Twomey.

The essistential part of laser diffraction instruments is the device for the registration of the scattered light pattern. Two different methods are being realized. In one setup, the scattered light pattern is focused by an objective on a multi-element detector and is registered there. This multi-element detector is e.g. a ring detector with concentric circular light sensitive segments. This detector converts the light, which is scattered to different angles, into electrical signals, which are associated to the individual angular zones of the scattered light, e.g. in a known design with a 32-element-detector. In another known setup, the scattered light pattern is focused on a plane where a rotating mask with several apertures is situated, which transmits light from different angular sections at different times. These apertures, e.g. rectangular apertures, are positioned at different radial distances from the axis. They are staggered in circumferential direction. The light transmitted through an aperture and through an additional stationary slit is focused on a one-element detector. Consequently, this detector registers at different times the light scattered into different angular sections.

Also other devices are known, where the objective is not arranged behind the cuvette or the assembly of particles, respectively, in front of the multi-element detector or the rotating mask, but between the light source and the cuvette or the assembly of particles, respectively. With this variant it is possible with simple means to detect the scattered light also at large angles.

The known devices have mainly three disadvantages.

They are complicated. If a multi-element detector is used, then each element of the detector is connected with electrical amplifier for the signal. If a rotating mask is used, then its actual angular position has to be monitored by additional electrical signals.

The devices known to date require a precise mechanical adjustment of the optical components. The optical axis of the arrangement (illumination-, focusing- and detection device) has to agree with high precision with the center of the multi-element detector or the rotating mask, respectively. In one known device this problem is solved by a motor-controlled adjustment.

The use of an objective requires that all rays which are scattered from the particles into one direction are focused to one single point in the focal plane. A rotationally symmetric pattern of scattered light is produced; from its angular scattered light distribution the particle size distribution can be computed, which produced this pattern. This requires, that the rotationally symmetric scattered light pattern must be concentric relative to the optical axis.

The devices known up to this time detect the scattered light intensity only at a restricted number of angles, e.g. 32 in the device with a 32-element detector. In other devices the number of angles is even less. Consequently, the available information for the computation of the particle size distribution is restricted, which can have negative effects on the accuracy of the computed particle size distribution from the scattered light pattern.

It is the object of the invention to provide a device of the above-mentioned kind which can be easily assembled and to provide a method for the determination of particle size distributions with higher accuracy, even if the distribution is broad or extended to the submicron range.

SUMMARY OF THE INVENTION

For the solution of this problem, the invention provides for the above-mentioned device, that the registration device is a video camera, that a Fraunhofer diffraction pattern of the particles is focused on the detector of this device, that the center of this pattern is determined by means of a computer from the digitized light intensities at the pixels of the detector and that the averaged radial intensity distribution of the scattered light distribution is computed and that the particle size distribution is computed from this radial intensity distribution. The invention provides for the above-mentioned device, that the registration device is a video camera, that a Fraunhofer diffraction pattern of the particles is focused on the detector of this device, that the center of this pattern is determined by means of a computer from the digitized light intensities at the pixels of the detector and that the averaged radial intensity distribution of the scattered light distribution is computed and that the particle size distribution is computed from this radial intensity distribution.

The video camera is preferably a CCD-camera (charge coupled device). As computer a universal computer is especially suited, especially a personal computer, loaded with the software for the analysis.

By using a video camera, esp. a CCD camera, surprisingly new advantages arise in comparison with known devices. Essential parts of the instument are an illumination device, usually consisting of a laserdiode with integrated beam expander, an objective and a video camera. The assembly of particles to be analysed is either in a suspension in a cuvette (with flowing or stationary suspension) or is transported through the instrument as an aerosol at the position where otherwise the cuvette is arranged. The assembly of particles, which is usually placed between illumination device and objective can also be placed between objective and video camera, especially in a convergent light beam, so that larger scattering angles and finer particles (size comparable to the wavelength of the light) can be registered.

The gray levels of the scattered light pattern registered by the video camera must be in a defined range for the faultless evaluation of the scattered light patterns by methods of image analysis. This is achieved by variation of the intensity of the laser light e.g. by direct variation of the light intensity emitted by the laser diode via adjustment of the voltage or the electrical current. A special alternative of the device according to the invention for the variation of the light intensity is a stepwise rotating disc with gray filters of different transmissivities. The positioning of the disc occurs preferably by a stepping motor. Instead of the variation of the light intensity by gray filters or by the variation of the voltage/current of the laser diode, the optimal recording-/registration of the scattered light pattern (optimal range of gray levels) can be achieved by the variation of the exposure time of the video camera, especially by an electronic shutter with adjustable exposure times.

The application of a video camera as a detector unit of the registration device for the analysis of the scattered light pattern allows a setup, where the axis of the illuminating light beam has not to be in the center of the detector. For the first time, scattered light patterns can be registered and analysed, if the light beam illuminates from different directions the assembly of particles, which may be in a cuvette. Therefore one embodiment of the invention provides that the direction of the coherent light beam illuminating the assembly of particles can be varied relative to the common optical axis of the objective and the video camera. For this purpose swivel/pivot-mounted reflecting surfaces, e.g. mirrors, can be arranged behind the illuminating device which direct the coherent light beam on the assembly of particles under a defined angle. The scattered light patterns received/registered by the video camera are always concentric to the axis of the light beam illuminating the suspension, even if this axis is far away from the video camera. The angle between the light beam illuminating the assembly of particles and the optical axis of the objective and the video camera shall be variable between 0 and more than 90 degrees. For the determination of a fine particle size distribution several exposures from different angles of the illuminating light beam are then necessary, where the number of the exposures is determined by the focal length of the objective. The resolution and the range of scattering angles can be varied independently by this method, which allows particle size analyses in the range from less than 0.2 micrometers to approximately 1 millimeter in one single measurement.

The scattered light pattern (Fraunhofer diffraction pattern) is registered by a video camera, esp. its CCD-chip, and, with known image processing methods, digitized, stored in a mass storage of a computer and mathematically analyzed via the solution of a Fredholm integral equation with a known algorithm. Preferably a personal computer with an integrated image processing board is used.

A suitable method is defined in the appended claims.

By the invention the following advantages are achieved:

The new device consists of only few components which are robust, most of them mass produced articles and therefore offer high quality at low costs.

The time consuming adjustment of the optical axis is not necessary because the center of the scattered light pattern is determined by image analysis methods.

The dependence of the scattered light intensity $I(\Theta)$ on the scattering angle $\Theta$ is also determined by methods of image analysis. By the variation of the angle between the axis of illumination and common optical axis of the objective and camera, the assembly of particles can be detected from different directions and therefore different sized fractions of particles can be determined. The detectable particle sizes are extended by this method to a range from 0.2 micrometers to 1 millimeter without the necessity of a change of the objective or of a shift of the cuvette in the direction of the optical axis. The spatial resolution is considerably higher than in known devices for scattered flight analysis, since the available detector devices (CCD-chips) have a much higher number of pixels and the resolution of these chips is being constantly improved.

The limited dynamic range of light intensities, in which the digitizing of the image can be performed, can be extended by different measurements of the same scattered light pattern but at different light levels. At high intensities of the illuminating beam, areas of relatively low intensity of the pattern can be measured precisely, which, however, implies that the bright areas are overexposed. The bright areas are measured at low illumination levels. From different exposures with different intensities of the illuminating light beam and with appropriate mathematical methods therefore a scattered light pattern $I(\Theta)$ can be detected which covers a large range of relative intensities.

The device is suitable for on-line particle size analyses, since the actual measurement occurs in fractions of a second and since the evaluation with a computer provides the result of a particle size analysis in a very short time. Additionally the device, like the known devices, does neither disturb the flow of the gas or liquid nor the particles.

Exemplary embodiments for the realization of a device according to the invention for the detection of the scattered light pattern are explained by means of the enclosed figures

BRIEF DESCRIPTION OF THE DRAWINGS

FIGS. 3a and 3b show the diagram of an averaged scattered light distribution of a narrow fraction of particles;

DETAILED DESCRIPTION OF THE INVENTION

Figure 1:
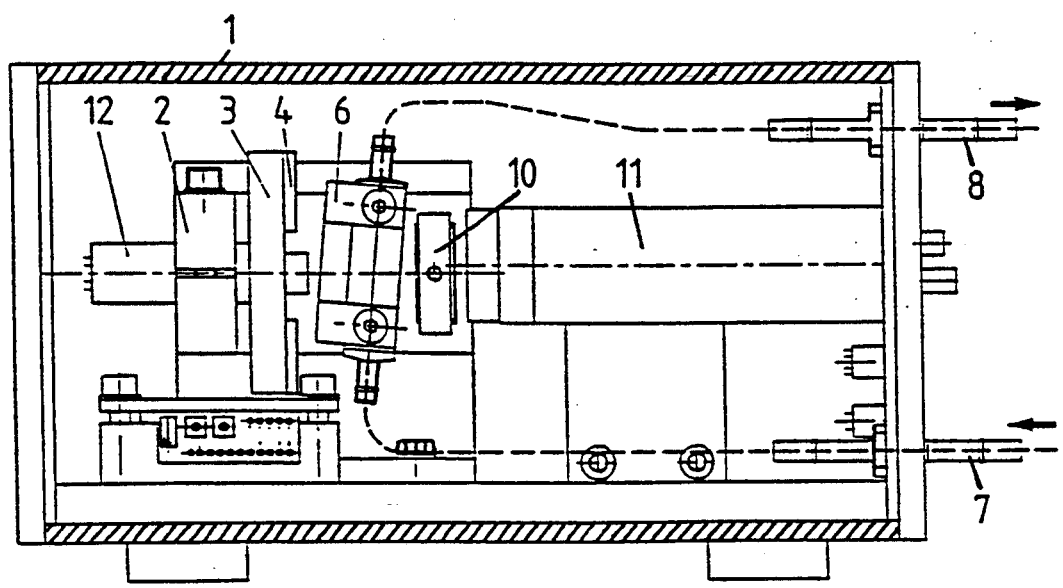
FIG. 1 is a sectional view of a device for the detection of the scattered light pattern.

The measuring device 1 according to FIG. 1 contains all essential components for the measurement. From this device, electrical signals are transmitted to a computer for further processing.

Along the optical axis an illumination unit with a laser diode 2 is arranged, further a beam expander, a rotating disc 3 with several gray filters 4 of different transmissivities, a cuvette 6 which is formed here as a flow-through cuvette through which a Suspension with the assembly of particles to be analysed is pumped and an objective 10 for the imaging of the scattered light pattern on a CCD video camera 11. A connection 7 is provided at a side wall of the device for the lower intake of the suspension into the flow-through cuvette 6 via a tube. a Similarly, a tube connects the upper outlet of the flow-through cuvette with the outlet connection 8 for the measured suspension. The disc 3 with the gray filters 4 is driven by a positioning motor 12 which is positioned next to the laser diode. In one example of a device, the laser diode has a wavelength of 670 nm. The light scattered by the assembly of particles is focused by means of the objective 10 on the CCD chip of the video camera 11.

Figure 7:
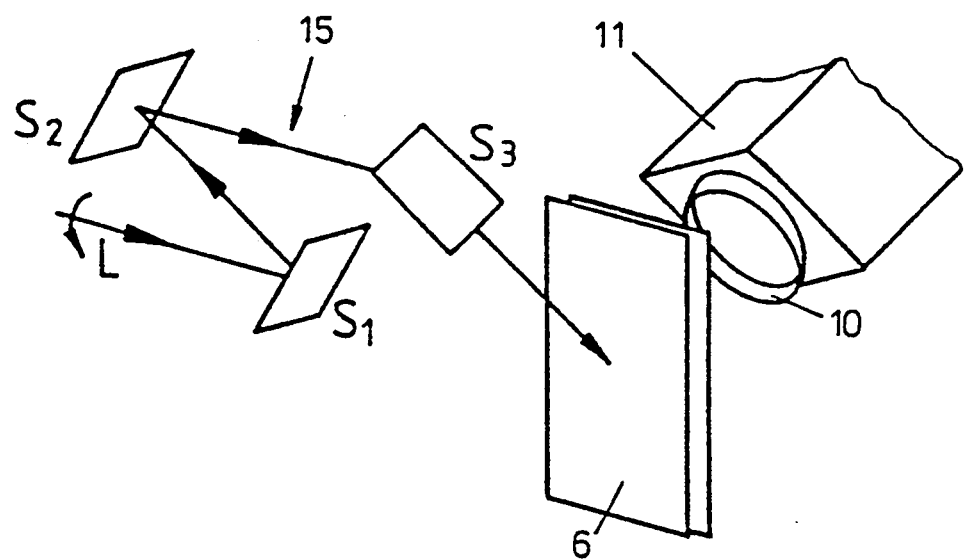
FIG. 7 is a sectional view of a modified device for the detection of the scattered light pattern with swivel-mounted mirrors between illumination unit and cuvette.
Figure 8:
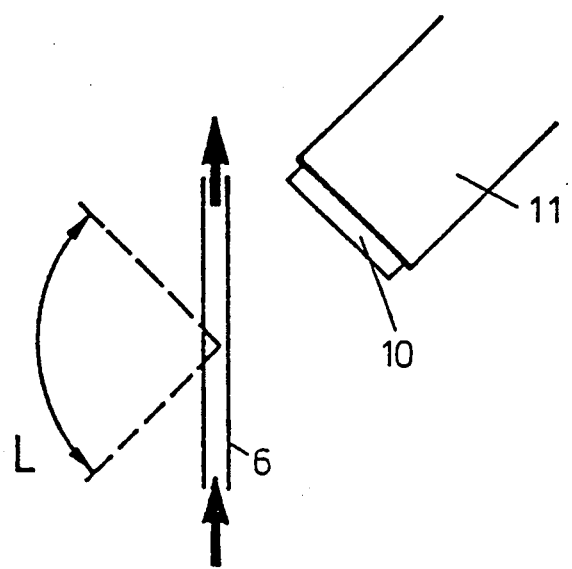
FIG. 8 is a plan view at the cuvette and the video camera with imaging optics (objective) to illustrate the range of the angle of the illuminating light beam.

In the design according to FIG. 7 the optical axis of the illumination unit is tilted to the axis of the objective and camera. This is achieved by an arrangement of reflecting surfaces 15 in front of the cuvette 6. It consists of 3 mirrors S1, S2 and S3. The parallel light beam L produced by the illumination unit impinges on the first mirror S1 and is derected from there via the mirrors S2 and S3 through the flow-through cuvette 6. The connection between the three mirrors is rigid. The unit 15 can be rotated about an axis which is parallel to the plane of the cuvette through which the light beam enters. FIG. 8 shows in a plan view the arrangement of the objective 10 and video camera 11 with respect to the flow-through cuvette 6. It can be seen that the angle between the light beam L which enters the cuvette and the optical axis of the objective 10 and the video camera 11 can be varied between 0 and 90 degrees. Depending on the entrance angle and the size of the particles different scattered light patterns result, from which the particle size distributions can be computed.

Several exposures from different entrance angles are necessary for an analysis. The number of exposures depends on the focal length of the objective. Therefore, the resolution and the range of scattering angles can be varied independently, which allows particle size analyses from the submicron range to about 1 millimeter in one single measurement without a change of the objective.

The new design of the measuring device 1 makes it possible to make it very small and to build it as a portable instrument. All parts which are essential for the measurement, including the computer and a power supply, can be mounted in a water-resistant case, which allows a mobile use of the portable instrument (Portable) under rough environmental conditions.

Figure 2:
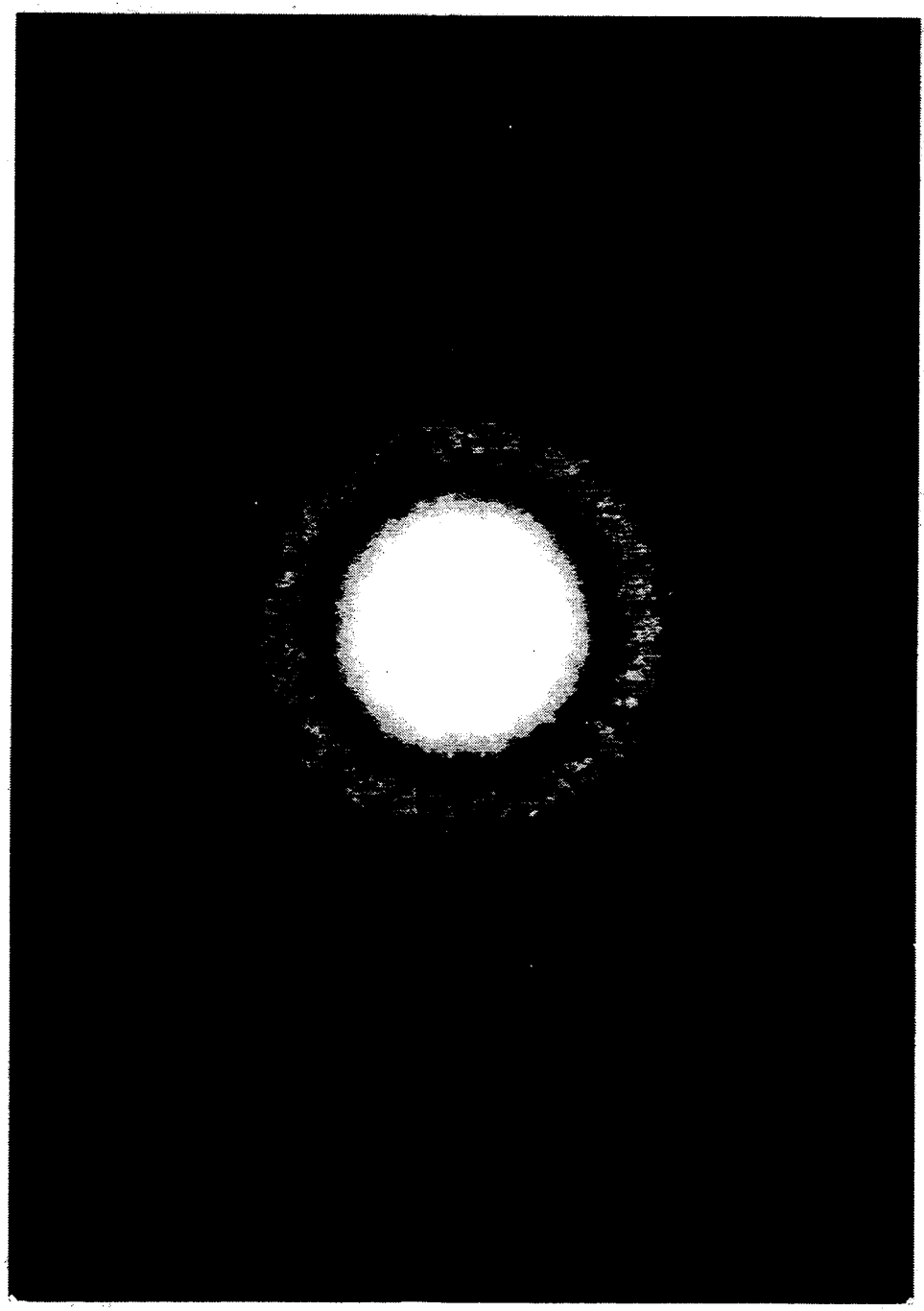
FIG. 2 is a rastered photography of a scattered light pattern.

The video camera, on whose CCD-chip the scattered light pattern is focused, produces an analog electrical signal which is digitized and stored in the computer. In order to determine the light intensity as a function of the scattering angle, it is first of all necessary to determine the exact coordinates of the center of the scattered light pattern. This task is accomplished in two steps. First, from the brightest line and column of the image a pixel A is determined, which is approximately the center, see FIG. 2. Starting from this point, the result is improved by an iterative and heuristic method. For that purpose, it is searched on orthogonal lines for points where the difference of gray values to the point A is higher than a certain value. Since not only the individual pixel is considered but the intensity is averaged over neighbored pixels, e.g. $5 \times 5$ pixels, noise can be suppressed in this step. The centers of the intervals between the found adjacent horizontal and vertical pixels are the X- and Y-coordinates of the improved solution for the center of the pattern, see point Z in FIG. 2.

The quality of this solution is mainly determined by the adjustment of the threshold to the given scattered light pattern. By comparison with the radial symmetry of the pattern, which is predicted from the theory for spherical particles, an automatic adaption of the threshold is possible. The search for pixels with appropriate differences of gray values is repeated with different thresholds, and the quality of the found final points is estimated by an evaluation function. This function describes how well a circle meets the four points. In this way it is possible to find the best solution in the sense of the evaluation function.

After the center of the scattered light pattern has been found, the radial light intensity distribution can be evaluated by averaging the intensities (gray values) at identical radii. In this way, noise, which may be superimposed to the pattern, can be suppressed effectively, since all pixels of the CCD-camera ($512 \times 768$ pixels) are considered.

If the intensity of scattered light, as a function of scattering angle, is known or stored in the computer, respectively, then the corresponding particle size distribution can be computed. The mathematical relation between the measured values, i.e. the scattered light intensity as a function of the scattering angle, is described in general by the Mie-theory, which, however, can be replaced under certain conditions by the Fraunhofer approximation. A Fredholm integral equation results.

A possible method for the solution of the Fredholm integral equation is the known approximation by a system of linear equations, which can be represented as matrix equation. By unavoidable inaccuracies in the measurement, however, this system may be unstable, which leads to varying results.

The coefficient-matrix which connects the vector of the measured values with the vector of the particle size distribution, has a strong influence on the stability of the solution of the system of equations The coefficient-matrix can be optimized by an appropriate choice of the particle size intervals for which the quantity of particles is determined, (division of intervals in a histogram) and for an appropriate choice of the angles, where the intensity of the scattered light pattern is evaluated. At larger superimposed errors, an optimization of the matrix alone is insufficient. The variations will become so large that a mathematical smoothing of the curve will be necessary which represents the results. Two smoothing methods are applicable:

1. The regularization according to Phillips and Twomey which represents a known method and which has been already successfully applied for the evaluation of diffracted light patterns and which renders possible a reduction of the sum of the absolute values of the curvatures of the curve which represents the results.
2. The weighted singular value decomposition which can be regarded as a low pass filter after a Fourier analysis.

Although both mathematical smoothing methods have no similarities, their results of smoothing are surprisingly narrow together. As the result $Q_3(x)$ resp. $Q_{3,smooth}(x)$ (the cumulative mass distribution os the particle size) is obtained.

Figure 4:
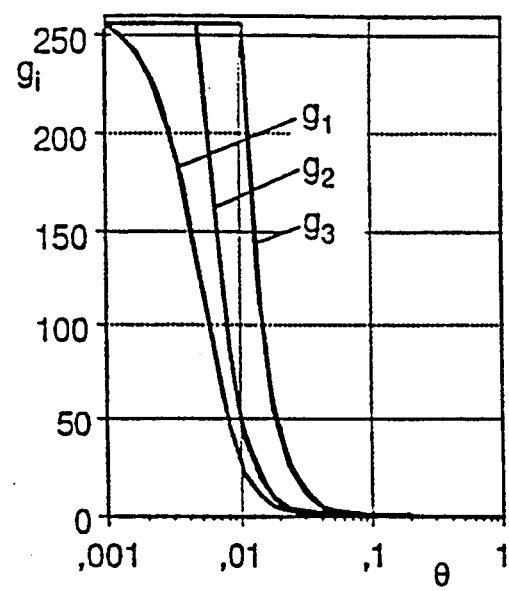
FIG. 4 shows several intensity distributions $g_i(\Theta)$.
Figure 5:
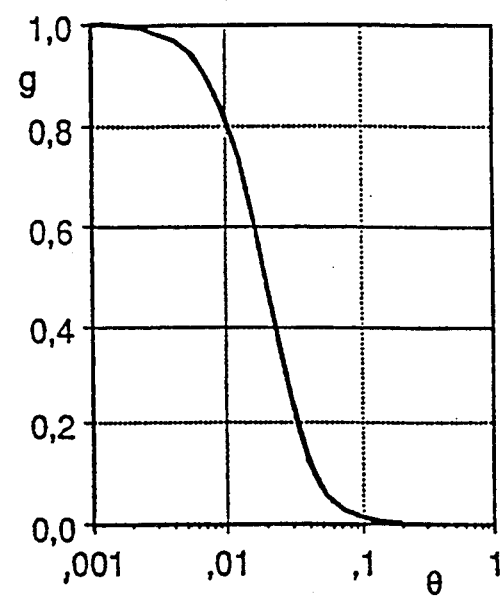
FIG. 5 shows an intensity distribution $g(\Theta)$, computed from the intensity distributions $g_i(\Theta)$ of FIG. 4.

The determination of several intensity distributions $g_i(t)$ at different intensities of the laser light $I_{0,i}$ is shown in FIG. 4. From this, the intensity distribution $g(\ominus)$ is computed, see FIG. 5.

The computation of the particle size distribution $q_3(x)$ from $g(\ominus)$ originates from the following equation:

$$g(\theta_k) = \sum_{i=1}^{n} \int_{a_i}^{a_{i+1}} \left( \frac{J_1(\theta_k \alpha)}{\theta_k \alpha} \right)^2 \alpha \, d\alpha \, q_i$$

$$\underbrace{\phantom{xxxxxxxx}}_{a_{ki}}$$

$$g_k = a_{k1} q_1 + a_{k2} q_2 + \ldots + a_{kn} q_n$$

where $g(\ominus)$ is the intensity distribution;
$\ominus$ is the scattering angle;
$\ominus_k (k=1, 2, \ldots n)$ are the angles at which the relative intensities $g(\ominus_k)$ of the scattered light have been measured and n is the total number of measurements;
$J_1$ is the Besselfunction of first kind and first order;
$\alpha$ is the Mie-Parameter $\alpha = \Pi x/\lambda$ where x is the particle size and $\lambda$ is the wavelength of light;
$q_i$ is the relative mass quantity of particles in the size interval between $x_i$ and $x_{i+1}$; and
Matrix formulation for m measured values $k=1,2,\ldots$ m $$g = Aq \rightarrow q = A^{-1}g$$

Generally a smoothing procedure is necessary because of the unavoidable errors in the measurement.

The equation for the Phillips-Twomey-Regularization with the smoothing parameter gamma is given by $$q_{3,smooth} = (A^T A + \gamma H)^{-1} A^T g$$

The equation for the singular value decomposition, $A = UWV^T$, weighted with the smoothing matrix F, is given by $$q_{3,smooth} = [V(F/W)U^T]g$$

Figure 6:
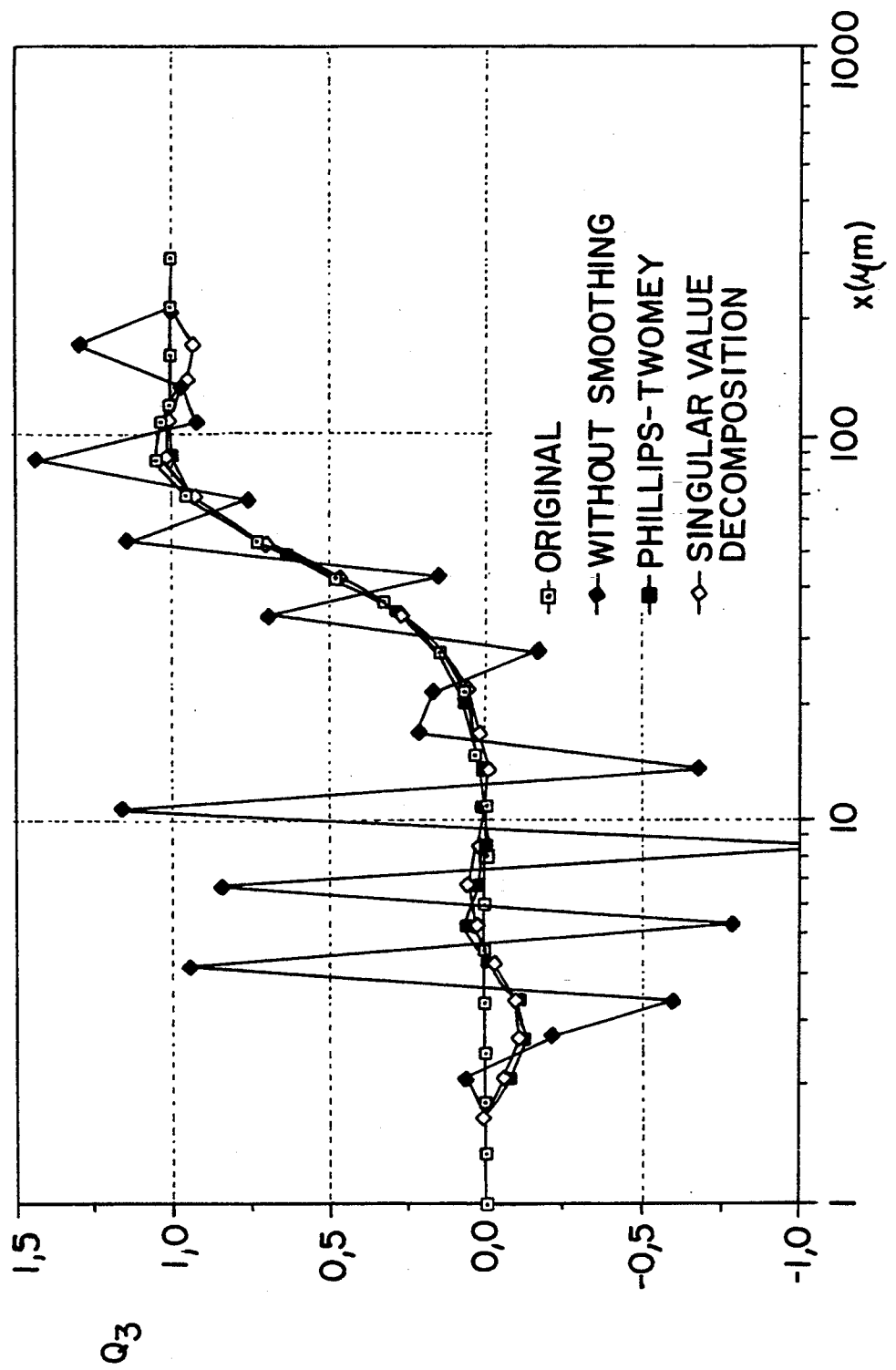
FIG. 6 depicts the computed particle size distributions as originally measured, without smoothing, with Phillips-Twomey regularization and with smoothing by singular value decomposition.

The result of the evaluation of the measurement and the smoothing by the Phillips Twomey regularisation resp. by the singular value decomposition is plotted as cumulative particle size distribution $Q_3(x)$ in FIG. 6.

We claim:

1. A device for determination of fine particle size distributions, comprising:

means for illuminating a suspended assembly of fine particles with coherent laser light of a predetermined intensity;

means for directing a Fraunhofer diffraction light pattern created by the illumination light scattered at the particles onto light-sensitive detector elements of a video camera to form a diffraction light pattern image on said detector elements, digitizing means for transformation of electrical light intensity signals generated by a detector element at each pixel of said diffraction light pattern image into digital signals, with said means for directing and said means for illuminating being adjacent; and computer means for computing from said digitized signals a point defining a center of the diffraction light pattern image and for determining therefrom an averaged radial intensity distribution of said diffraction light pattern image via solution of a Fredholm integral equation and for computing the particle size distribution of said suspended assembly.

2. The device as claimed in claim 1 wherein the video camera is a CCD-camera.

3. The device as claimed in claim 1 wherein said computer is a personal computer, into which an evaluation program comprising an algorithm for said digitized signals at said pixels is loaded as software.

4. The device as claimed in claim 1 wherein a stepwise rotating disc with gray filters of different transmissivities is positioned between said coherent light illuminating means and said assembly of suspended particles to vary an intensity of illumination of said particles.

5. The device as claimed in claim 1 wherein said video camera has variable exposure time.

6. The device as claimed in claim 1 wherein a direction of said coherent light, which illuminates the assembly of particles, can be varied relative to an optical axis of said means for directing the video camera.

7. The device as claimed in claim 6, wherein said coherent light is directed in a predetermined angle upon the assembly of particles by a pivotally mounted arrangement of reflecting surfaces.

8. The device as claimed in claim 6 wherein an angle between a direction of extension of the assembly of particles and said optical axis of said means for directing the video camera is variable between 0 and 90 degrees.

9. The device as claimed in claim 1 wherein an image processing board is integrated in the computer.

10. The device as claimed in claim 1 wherein all components of the device, including the computer and a power supply, are assembled in a waterproof casing as a portable instrument.

11. A method for determination of fine particle size distributions, comprising:

illuminating an assembly of suspended fine particles with coherent laser light to create a Fraunhofer diffraction pattern of light scattered by the particles;

providing a video camera with a light-sensitive detector element;

directing said Fraunhofer diffraction light pattern onto said light-sensitive detector element of said video camera and generating electrical light intensity signals at each pixel of the diffraction light pattern image;

digitizing said electrical light intensity signals generated by said detector element to form digital signals;

computing from said digitized signals a point defining a center of the diffraction light pattern image;

determining therefrom an averaged radial intensity distribution of said scattered light pattern via solution of a Fredholm integral equation; and computing therefrom the particle size distribution of said suspended assembly.

12. The method as claimed in claim 11 wherein for registration of said diffracted light pattern an angle between a coherent light beam entering the assembly of particles and an optical axis of an imaging device can be varied incrementally.

13. The method of claim 11 wherein a direction of coherent light, which illuminates said assembly of particles, can be varied relative to an optical axis of said video camera.

* * * * *

UNITED STATES PATENT AND TRADEMARK OFFICE
CERTIFICATE OF CORRECTION

PATENT NO. : 5,438,408
DATED : August 1, 1995
INVENTOR(S) : Reiner Weichert and Wolfgang Witt Page 1 of 3

It is certified that error appears in the above-indentified patent and that said Letters Patent is hereby corrected as shown below:

Column 1 Line 18 "signals," should read --signals.--.

Column 1 Line 44 "essistential" should read --essential--.

Column 2 Line 8 after "with" insert --an--.

Column 2 Line 24 after "requires" delete ",".

Column 4 Line 55-Column 5 Line 12 relocate the text beginning with "BRIEF DESCRIPTION OF THE DRAWINGS" and ending with "DETAILED DESCRIPTION OF THE INVENTION" to Column 2 Line 54 after the sentence ending with "distribution." Begin a new paragraph under "BRIEF DESCRIPTION OF THE DRAWINGS" with "The invention".

Column 4 Line 27 "flight" should read --light--.

Column 4 Line 54 after "figures" insert --.--.

UNITED STATES PATENT AND TRADEMARK OFFICE
CERTIFICATE OF CORRECTION

PATENT NO. : 5,438,408
DATED : August 1, 1995
INVENTOR(S) : Reiner Weichert and Wolfgang Witt It is certified that error appears in the above-indentified patent and that said Letters Patent is hereby corrected as shown below:

Column 5 Line 21 "Suspension" should read --suspension--.

Column 5 Lines 26-27 "a Similarily," should read --Similarly,--.

Column 5 Line 42 "derected" should read --directed--.

Column 6 Line 61 after "equations" insert --.--.

Column 7 Line 17 "os" should read --of--.

Column 7 Line 20 "gi(t)" should read --$g_i(\theta)$--.

Column 7 Lines 25-32

$$" \; g(\theta_k) = \sum_{i=1}^{n} \underbrace{\int_{\alpha_i}^{\alpha_i \cdot 1} \left( \frac{J_1(\theta_k \alpha)}{\theta_k \alpha} \right)^2 \alpha \, d\alpha}_{a_{ki}} \; q_i \; "$$

should read $$-- \; g(\theta_k) = \sum_{i=1}^{n} \underbrace{\int_{\alpha_i}^{\alpha_i \cdot 1} \left( \frac{J_1(\theta_k \alpha)}{\theta_k \alpha} \right)^2 \alpha \, d\alpha}_{a_{ki}} \; q_i \; \Rightarrow --.$$

UNITED STATES PATENT AND TRADEMARK OFFICE
CERTIFICATE OF CORRECTION

PATENT NO. : 5,438,408
DATED : August 1, 1995
INVENTOR(S) : Reiner Weichert and Wolfgang Witt It is certified that error appears in the above-indentified patent and that said Letters Patent is hereby corrected as shown below:

Claim 7 Line 39 Column 8 after "6" delete ",".

Signed and Sealed this

Twelfth Day of March, 1996

Attest:

BRUCE LEHMAN

Attesting Officer

Commissioner of Patents and Trademarks

UNITED STATES PATENT AND TRADEMARK OFFICE
CERTIFICATE OF CORRECTION

PATENT NO. : 5,438,408
DATED : August 1, 1995
INVENTOR(S) : Reiner Weichert and Wolfgang Witt It is certified that error appears in the above-indentified patent and that said Letters Patent is hereby corrected as shown below:

On the title page, item [57]

Abstract Line 17 "transmittivities" should read --transmissivities--.

Column 1 Line 18 "signals," should read --signals.--.

Column 1 Line 44 "essistential" should read --essential--.

Column 2 Line 8 after "with" insert --an--.

Column 2 Line 24 after "requires" delete ",".

Column 4 Line 55-Column 5 Line 12 relocate the text beginning with "BRIEF DESCRIPTION OF THE DRAWINGS" and ending with "DETAILED DESCRIPTION OF THE INVENTION" to Column 2 Line 54 after the sentence ending with "distribution." Begin a new paragraph under "BRIEF DESCRIPTION OF THE DRAWINGS" with "The invention".

Column 4 Line 27 "flight" should read --light--.

Column 4 Line 54 after "figures" insert --.--.

UNITED STATES PATENT AND TRADEMARK OFFICE
CERTIFICATE OF CORRECTION

PATENT NO. : 5,438,408
DATED : August 1, 1995
INVENTOR(S) : Reiner Weichert and Wolfgang Witt It is certified that error appears in the above-indentified patent and that said Letters Patent is hereby corrected as shown below:

Column 5 Line 21 "Suspension" should read --suspension--.

Column 5 Lines 26-27 "a Similarily," should read --Similarly,--.

Column 5 Line 42 "derected" should read --directed--.

Column 6 Line 61 after "equations" insert --.--.

Column 7 Line 17 "os" should read --of--.

Column 7 Line 20 "gi(t)" should read --$g_i(\theta)$--.

Column 7 Lines 25-32

$$\text{`` } g(\theta_k) = \sum_{i=1}^{n} \underset{a_{ki}}{\int_{\alpha_i}^{\alpha_{i+1}} \left( \frac{J_1(\theta_k \alpha)}{\theta_k \alpha} \right)^2 \alpha \, d\alpha} \; q_i \text{ ''}$$

should read $$\text{-- } g(\theta_k) = \sum_{i=1}^{n} \underbrace{\int_{\alpha_i}^{\alpha_{i+1}} \left( \frac{J_1(\theta_k \alpha)}{\theta_k \alpha} \right)^2 \alpha \, d\alpha}_{a_{ki}} \; q_i \;\; \Rightarrow \text{ --.}$$

UNITED STATES PATENT AND TRADEMARK OFFICE
CERTIFICATE OF CORRECTION

PATENT NO. : 5,438,408
DATED : August 1, 1995
INVENTOR(S) : Reiner Weichert and Wolfgang Witt It is certified that error appears in the above-indentified patent and that said Letters Patent is hereby corrected as shown below:

Claim 7 Line 39 Column 8 after "6" delete ",".

This certificate supersedes Certificate of Correction issued March 12, 1996.

Signed and Sealed this

Twenty-third Day of July, 1996

BRUCE LEHMAN

*Attest:*

*Attesting Officer*          *Commissioner of Patents and Trademarks*

UNITED STATES PATENT AND TRADEMARK OFFICE
CERTIFICATE OF CORRECTION

PATENT NO. : 5,438,408  
DATED : August 1, 1995  
INVENTOR(S) : Reiner Weichert and Wolfgang Witt Page 1 of 1

It is certified that error appears in the above-identified patent and that said Letters Patent is hereby corrected as shown below:

<u>Column 2,</u>  
Line 3, after "image" insert comma -- , --.

Signed and Sealed this

Thirtieth Day of April, 2002

*Attest:*

*Attesting Officer*

JAMES E. ROGAN  
*Director of the United States Patent and Trademark Office*

UNITED STATES PATENT AND TRADEMARK OFFICE
CERTIFICATE OF CORRECTION

PATENT NO. : 5,438,408 C1
DATED : August 1, 1995
INVENTOR(S) : Reiner Weichert and Wolfgang Witt It is certified that error appears in the above-identified patent and that said Letters Patent is hereby corrected as shown below:

Column 2,
Line 3, after "image" insert comma -- , --.

This certificate supersedes Certificate of Correction issued April 30, 2002, for patent number 5,438,408.

Signed and Sealed this

Fourteenth Day of January, 2003

Attest:

Attesting Officer

JAMES E. ROGAN
Director of the United States Patent and Trademark Office

(12) REEXAMINATION CERTIFICATE (4427th)
United States Patent
Weichert et al.

(10) Number: US 5,438,408 C1
(45) Certificate Issued: Aug. 28, 2001

(54) MEASURING DEVICE AND METHOD FOR THE DETERMINATION OF PARTICLE SIZE DISTRIBUTIONS BY SCATTERED LIGHT MEASUREMENTS

(75) Inventors: Reiner Weichert; Wolfgang Witt, both of Clausthal-Zellerfeld (DE)

(73) Assignee: Sympatec GmbH System-Partikel-Technik, Clausthal-Zellerfeld (DE)

Reexamination Request:
No. 90/005,077, Aug. 19, 1998

Reexamination Certificate for:
Patent No.: 5,438,408
Issued: Aug. 1, 1995
Appl. No.: 07/983,559
Filed: Feb. 5, 1993

Certificate of Correction issued Mar. 12, 1996.

Certificate of Correction issued Jul. 23, 1996.

(22) PCT Filed: Jun. 5, 1992
(86) PCT No.: PCT/EP92/01276
§ 371 Date: Feb. 25, 1993
§ 102(e) Date: Feb. 25, 1993
(87) PCT Pub. No.: WO92/21955
PCT Pub. Date: Dec. 10, 1992

(51) Int. Cl.⁷ .................................................. G01N 15/02
(52) U.S. Cl. .......................................... 356/336; 356/337
(58) Field of Search .................................... 356/336–343

(56) References Cited

U.S. PATENT DOCUMENTS

| | | |
|---|---|---|
| 3,659,946 | 5/1972 | Kozawa et al. . |
| 3,830,969 * | 8/1974 | Hofstein ............................. 356/335 |
| 4,320,462 | 3/1982 | Lund et al. . |
| 4,335,405 | 6/1982 | Sakane et al. . |
| 4,409,470 | 10/1983 | Shepard et al. . |
| 4,439,726 | 3/1984 | Van Vliet et al. . |
| 4,460,836 | 7/1984 | Tsunekawa et al. . |
| 4,606,635 | 8/1986 | Miyazawa et al. . |
| 4,676,641 | 6/1987 | Bott . |
| 4,755,052 | 7/1988 | Giglio et al. . |
| 4,803,652 | 2/1989 | Maeser et al. . |
| 4,895,446 | 1/1990 | Maldari et al. . |
| 4,953,978 | 9/1990 | Bott et al. . |
| 5,007,737 | 4/1991 | Hirleman, Jr. . |
| 5,135,306 | 8/1992 | Kanebako et al. . |
| 5,185,641 | 2/1993 | Igushi et al. . |
| 5,576,827 | 11/1996 | Strickland et al. . |

OTHER PUBLICATIONS

Hirleman, et al., *Adaptive Fraunhofer Diffraction Particle Sizing Instrument Using A Spatial Light Modulator*, Applied Optics, No. 15, 1989, vol. 28, No. 22, pp. 4870–4878.

(List continued on next page.)

*Primary Examiner*—David Hardy

(57) ABSTRACT

For the determinatin of fine particle size distributions by scattered light measurements, an assembly of suspended particles is illuminated with coherent light, the scattered light pattern is focused on a light sensitive multi-element detector of a registration device and is transformed there to electrical signals. From the digitized electrical signals, the particle size distribution is computed with a computer. For the simplification of the setup and for the improvement of the accuracy of the computable particle size distribution, it is provided that the registration device is a video camera and that the particle size distribution is computed via the solution of a Fredholm integral equation from the signals produced by the light intensities at the pixels of the video camera. The video camera is a CCD camera. For the variation of the brightness, a rotating disc with gray filters of different transmittivities is provided in the measuring light beam, or the camera is equipped with an electronic shutter for different exposure times. Different fractions of particle sizes is measured also by variation of the angle between the optical axes of illumination and imaging devices.

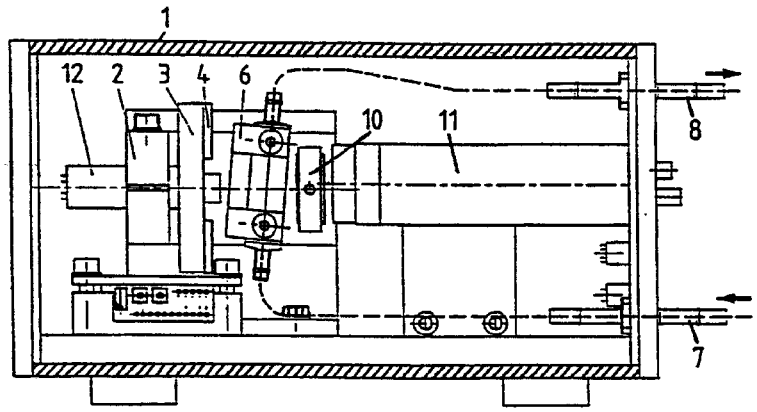

OTHER PUBLICATIONS

Bayvel, et al., *Optical Instrument for Monitoring the Particle Size Distribution in the Range 0.1–1000 µm,* World Congress Particle Technology, Part I: Particle Characterization, Nurnberg, 1986, pp. 155–164.

H.G. Barth, *Modern Methods of Particle Size Analysis,* Chemical Analysis, 1984, vol. 73, pp. 56–57.

Christian Buil, *CCD Astronomy,* William–Bell, Inc., 1989, pp. 153, 176–177, 204–205, 258–261.

N. Lightfoot and D. J. Watson, *Laser Diffraction Particle Size Analysis,* Particle Technology Conference, University of New South Wales, Australia, 1989, pp. 4–5.

* cited by examiner

US 5,438,408 C1

REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

Claims 1, 6 and 11 are determined to be patentable as amended.

Claims 2–5, 7–10, 12 and 13, dependent on an amended claim, are determined to be patentable.

1. A device for determination of fine particle size distributions, comprising:
   means for illuminating a suspended assembly of fine particles with coherent laser light of a predetermined intensity;
   means for directing a Fraunhofer diffraction light pattern created by the illumination light scattered at the particles onto light-sensitive detector elements of a video camera *in a video camera* to form a diffraction light pattern image on said detector elements,
   digitizing means for transformation of electrical light intensity signals generated by a detector element at each pixel of said diffraction light pattern image into digital signals,
   with said means for directing and said means for illuminating being adjacent; and
   computer means for computing from said digitized signals a point defining a center of the diffraction light pattern image and for determining therefrom an averaged radial intensity distribution of said diffraction light pattern image via solution of a Fredholm integral equation and for computing the particle size distribution of said suspended assembly.

6. The device as claimed in claim 1 wherein a direction of said coherent light, which illuminates the assembly of particles, can be varied relative to an optical axis of said means for directing *and* the video camera.

11. A method for determination of fine particle size distributions, comprising:
    illuminating an assembly of suspended fine particles with coherent laser light to create a Fraunhofer diffraction pattern of light scattered by the particles;
    providing a video camera with a light-sensitive detector element;
    directing said Fraunhofer diffraction light pattern onto said light-sensitive detector element of said video camera *in said video camera* and generating electrical light intensity signals at each pixel of the diffraction light pattern image;
    digitizing said electrical light intensity signals generated by said detector element to form digital signals;
    computing from said digitized signals a point defining a center of the diffraction light pattern image;
    determining therefrom an averaged radial intensity distribution of said scattered light pattern via solution of a Fredholm integral equation; and
    computing therefrom the particle size distribution of said suspended assembly.

* * * * *